(12) United States Patent
Farrell

(10) Patent No.: US 11,596,703 B2
(45) Date of Patent: Mar. 7, 2023

(54) PERSONAL PROTECTIVE EQUIPMENT SANITIZING ASSEMBLY

(71) Applicant: John Farrell, Brooklyn Park, MN (US)

(72) Inventor: John Farrell, Brooklyn Park, MN (US)

(*) Notice: Subject to any disclaimer, the term of this patent is extended or adjusted under 35 U.S.C. 154(b) by 342 days.

(21) Appl. No.: 17/010,936

(22) Filed: Sep. 3, 2020

(65) Prior Publication Data
US 2022/0062482 A1 Mar. 3, 2022

(51) Int. Cl.
*A61L 2/10* (2006.01)
*A61L 2/26* (2006.01)
*A47B 49/00* (2006.01)
*A47B 81/00* (2006.01)

(52) U.S. Cl.
CPC .............. *A61L 2/26* (2013.01); *A47B 49/004* (2013.01); *A47B 49/008* (2013.01); *A47B 81/00* (2013.01); *A61L 2/10* (2013.01); *A61L 2202/11* (2013.01); *A61L 2202/26* (2013.01)

(58) Field of Classification Search
CPC ... A61L 2/10; A61L 2202/122; A47B 49/004; A47B 49/008
See application file for complete search history.

(56) References Cited

U.S. PATENT DOCUMENTS

| 5,160,699 A | 11/1992 | Siegal |
| 6,593,131 B2 | 7/2003 | Ta |
| 2003/0034459 A1 | 2/2003 | Bonin |
| 2006/0263275 A1 | 11/2006 | Lobach |
| 2010/0266445 A1 | 10/2010 | Campagna |
| 2021/0299304 A1* | 9/2021 | Concannon ............... A61L 2/26 |

* cited by examiner

*Primary Examiner* — Eliza W Osenbaugh-Stewart

(57) ABSTRACT

A personal protective equipment sanitizing assembly includes a cabinet that is comprised of a translucent material to pass light therethrough. An upper door is hingedly coupled to the cabinet and a lower door is hingedly coupled to the cabinet. A cart is rollably positioned in the cabinet and the cart is rollable onto the lower door when the lower door is opened for accessing the cart. A carousel unit is rotatably coupled to the cart and the carousel unit includes a plurality of suspensions to support a respective one of a plurality of face masks or other personal protective equipment. A plurality of light emitters is each coupled to the cart to emit light onto the carousel unit. Each of the light emitters has an operational wavelength ranging between approximately 10.0 nm and 400.0 nm for sterilizing the face masks.

14 Claims, 7 Drawing Sheets

PERSONAL PROTECTIVE EQUIPMENT SANITIZING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to sanitizing device and more particularly pertains to a new sanitizing device for sanitizing personal protective equipment.

(2) Description of Related Art Including Information Disclosed Under 37 CFR 1.97 and 1.98

The prior art relates to sanitizing devices including a cabinet with ultraviolet light emitters for sterilizing eyewear. Additionally, the prior art discloses a sterilizing cabinet that includes ultraviolet light emitters and a plurality of shelves for sterilizing cultivated cultures. The prior art also discloses a variety of cabinets that each has an ultraviolet light emitter for sterilizing objects.

BRIEF SUMMARY OF THE INVENTION

An embodiment of the disclosure meets the needs presented above by generally comprising a cabinet that is comprised of a translucent material to pass light therethrough. An upper door is hingedly coupled to the cabinet and a lower door is hingedly coupled to the cabinet. A cart is rollably positioned in the cabinet and the cart is rollable onto the lower door when the lower door is opened for accessing the cart. A carousel unit is rotatably coupled to the cart and the carousel unit includes a plurality of suspensions to support a respective one of a plurality of face masks or other personal protective equipment. A plurality of light emitters is each coupled to the cart to emit light onto the carousel unit. Each of the light emitters has an operational wavelength ranging between approximately 10.0 nm and 400.0 nm for sterilizing the face masks.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
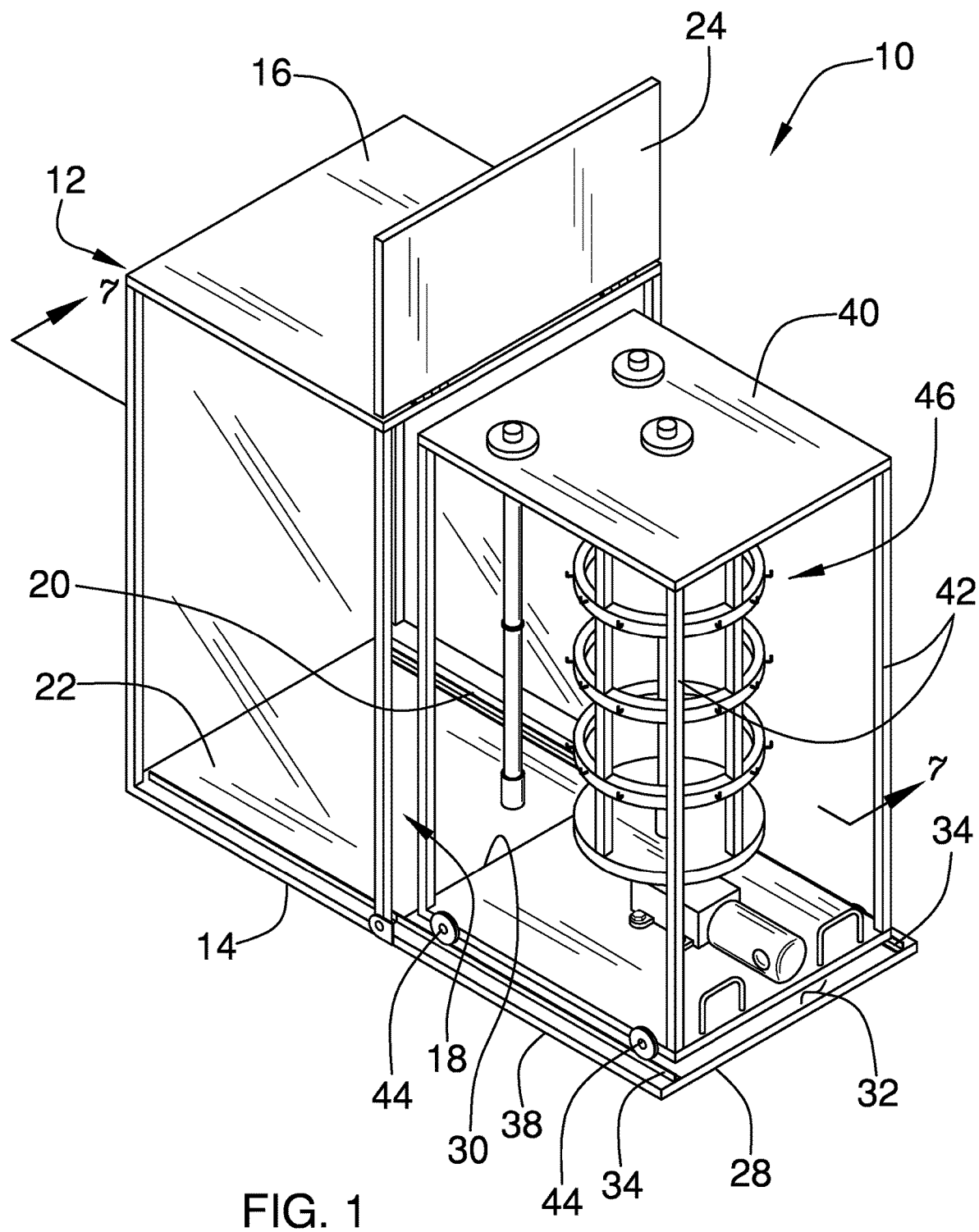
FIG. 1 is a perspective view of a personal protective equipment sanitizing assembly according to an embodiment of the disclosure.
Figure 2:
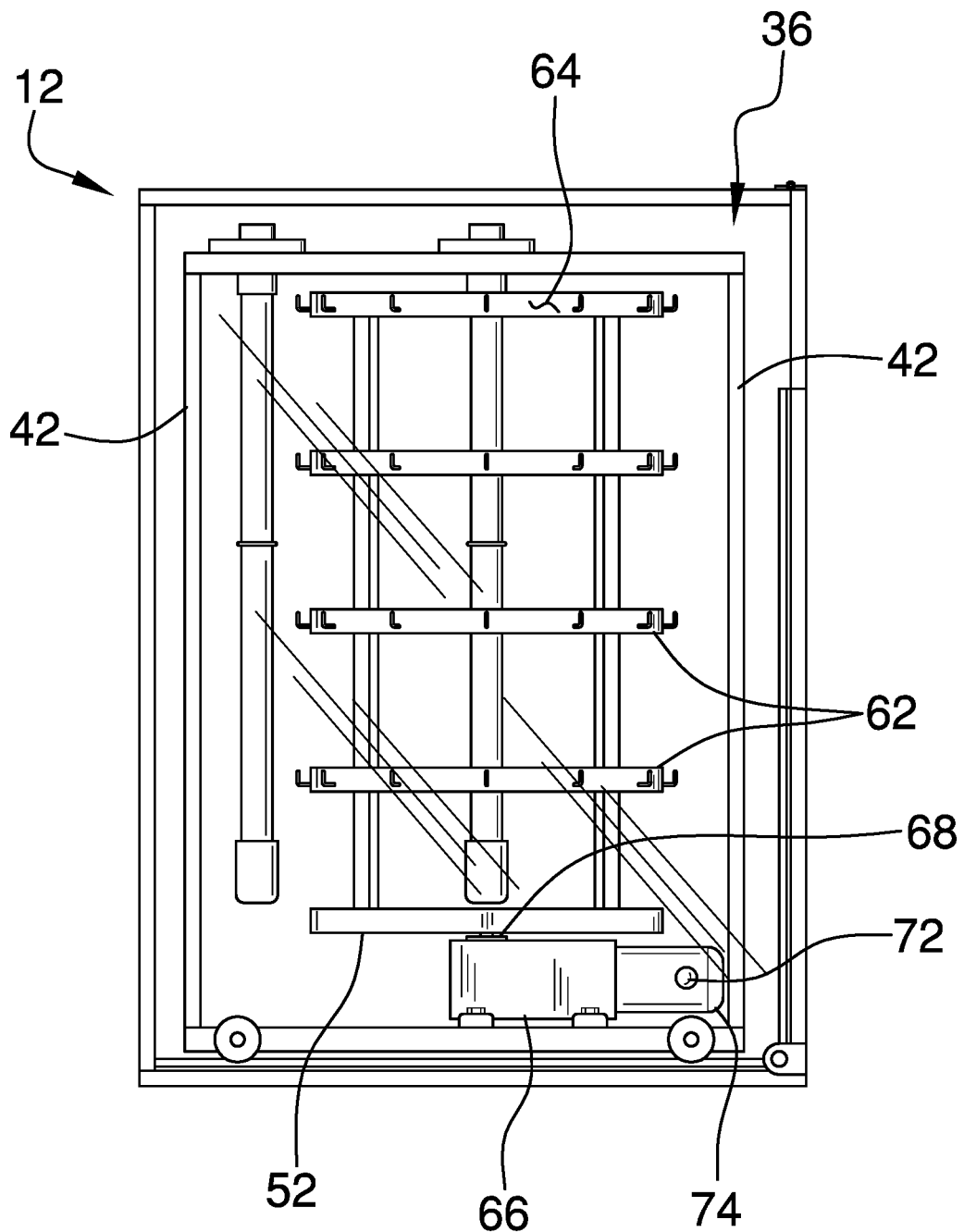
FIG. 2 is a right side view of an embodiment of the disclosure.
Figure 3:
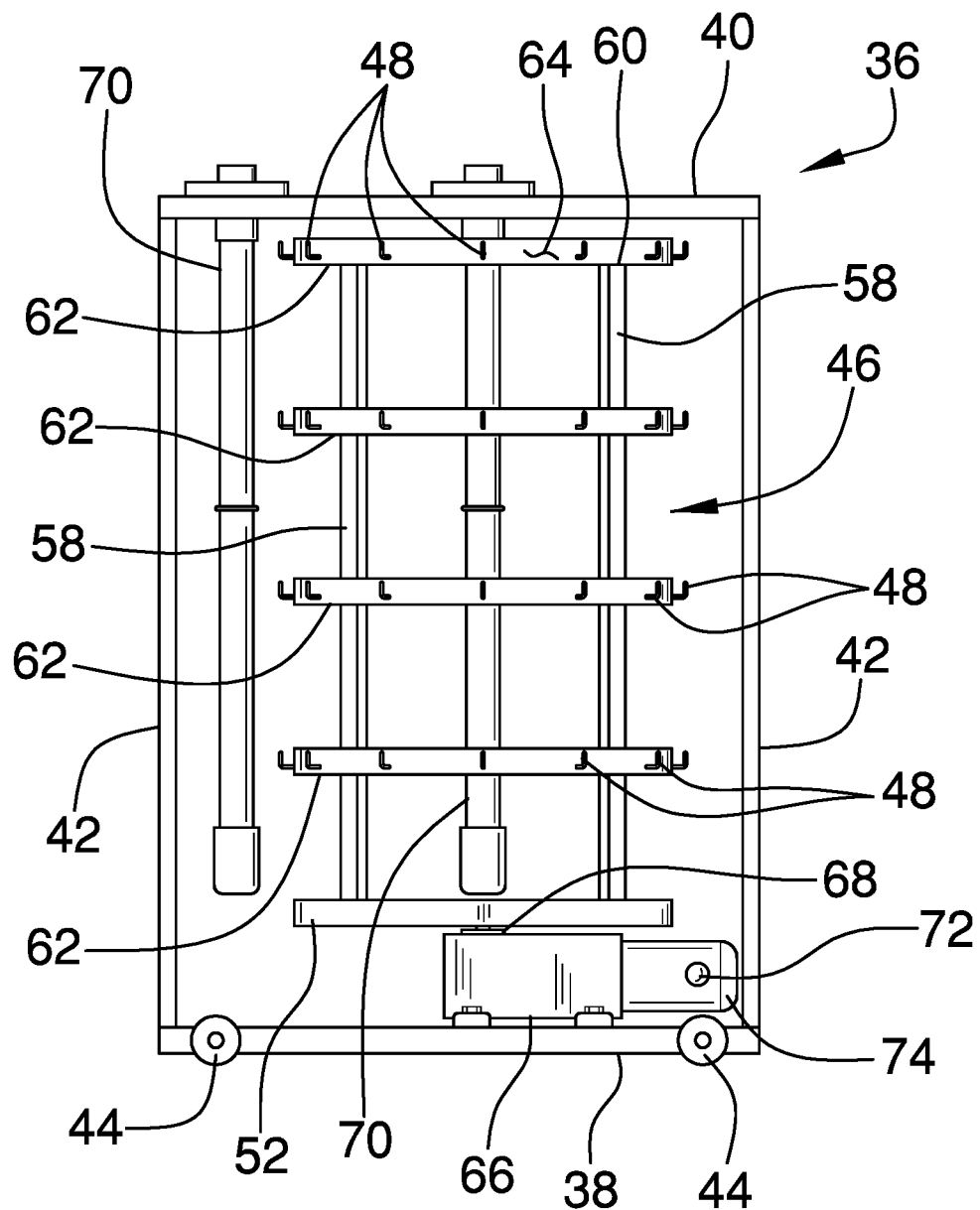
FIG. 3 is a right side view of a cart and a carousel unit of an embodiment of the disclosure.
Figure 4:
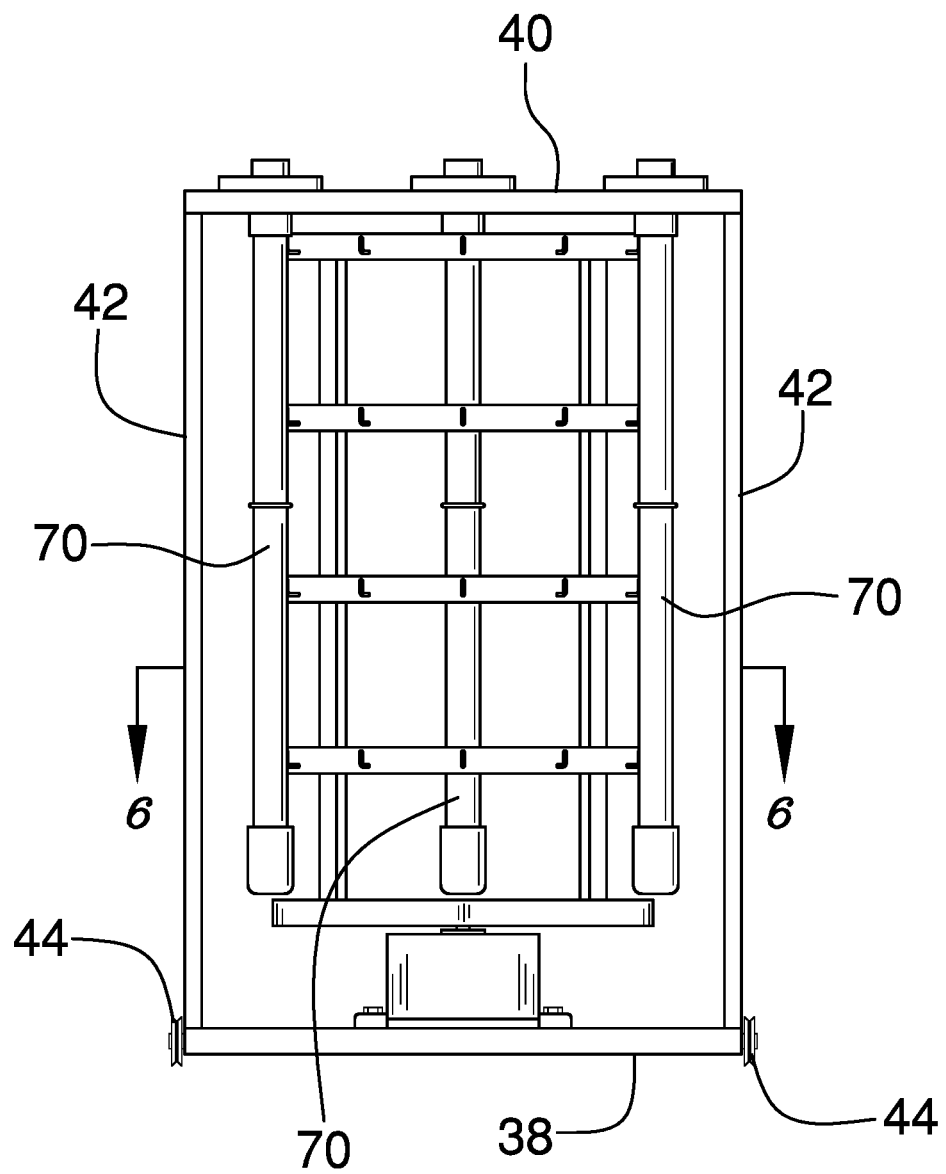
FIG. 4 is a front view of a cart and a carousel unit of an embodiment of the disclosure.
Figure 5:
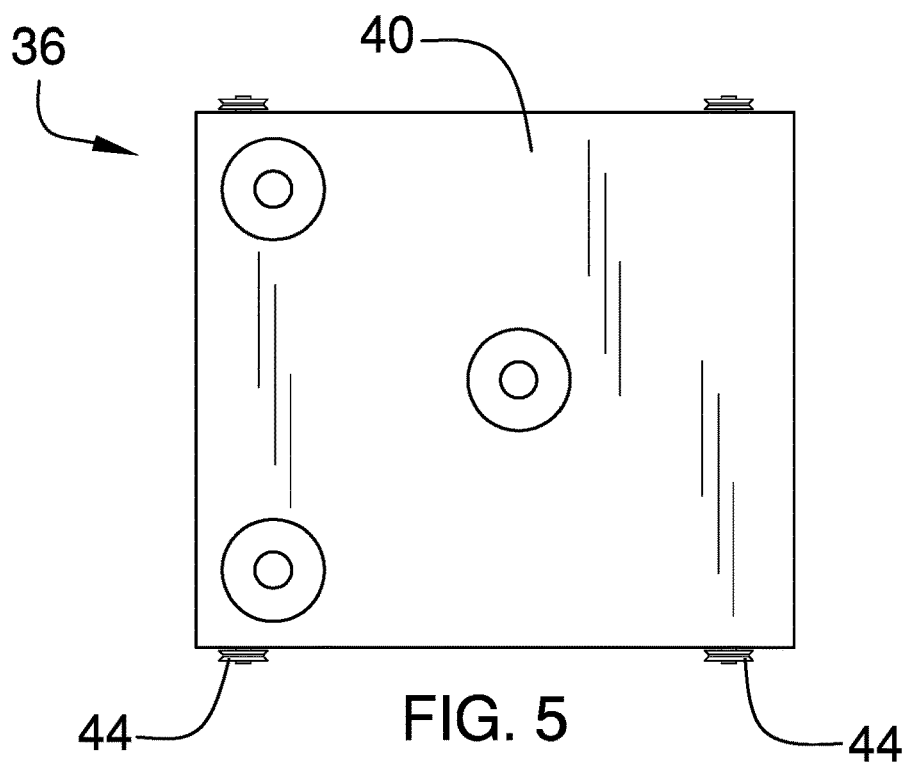
FIG. 5 is a top view of an embodiment of the disclosure.
Figure 6:
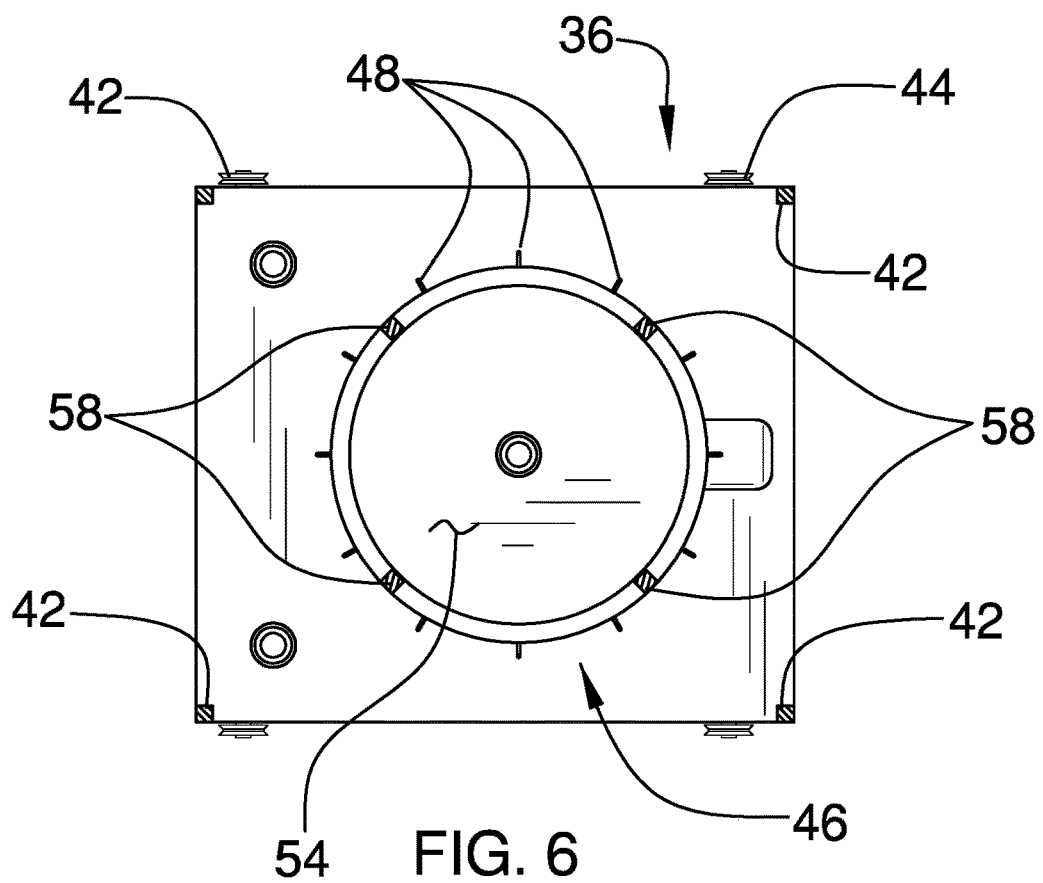
FIG. 6 is a cross sectional view taken along line 6-6 of FIG. 4 of an embodiment of the disclosure.
Figure 7:
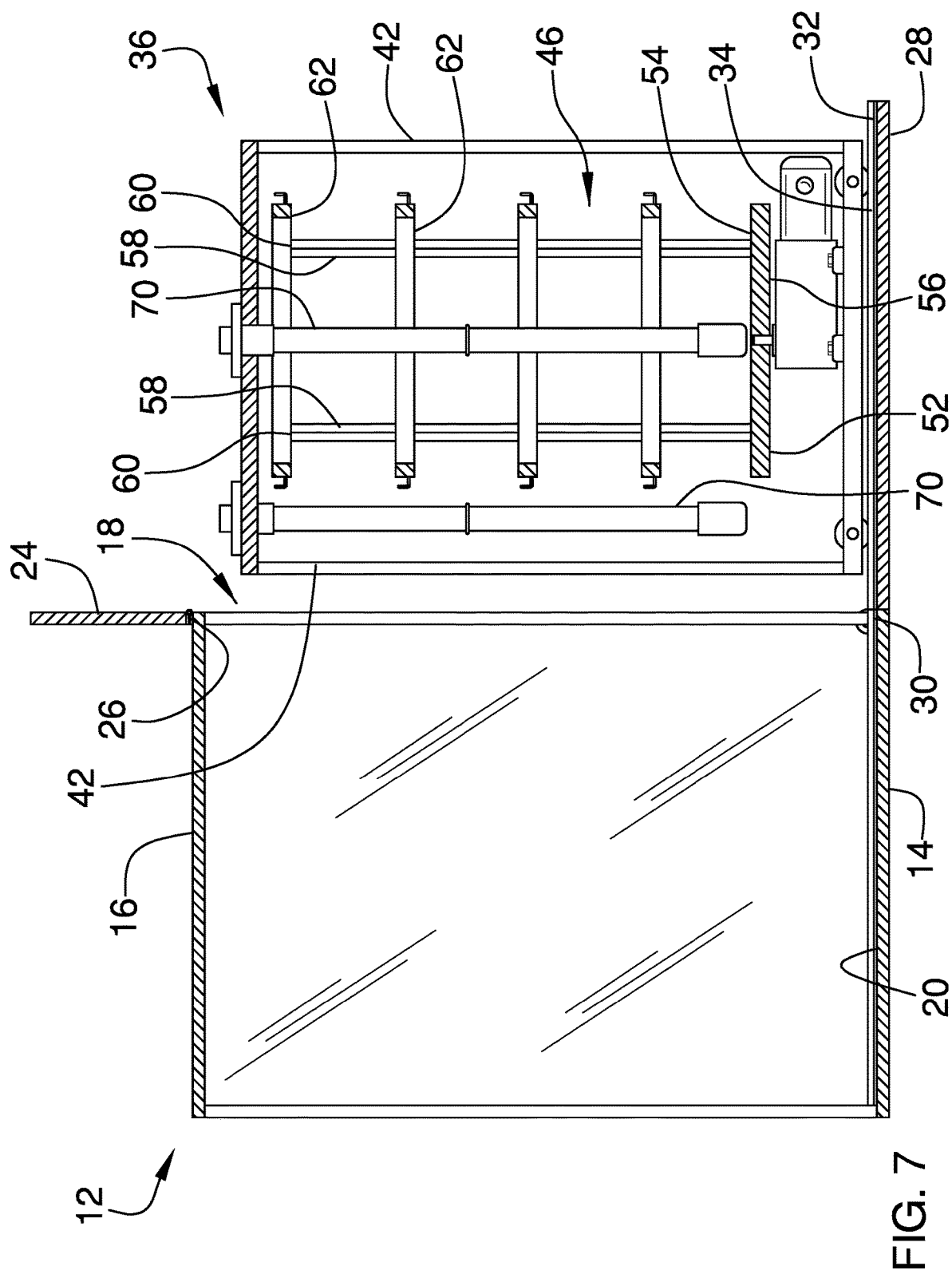
FIG. 7 is a cross sectional view taken along line 7-7 of FIG. 1 of an embodiment of the disclosure.
Figure 8:
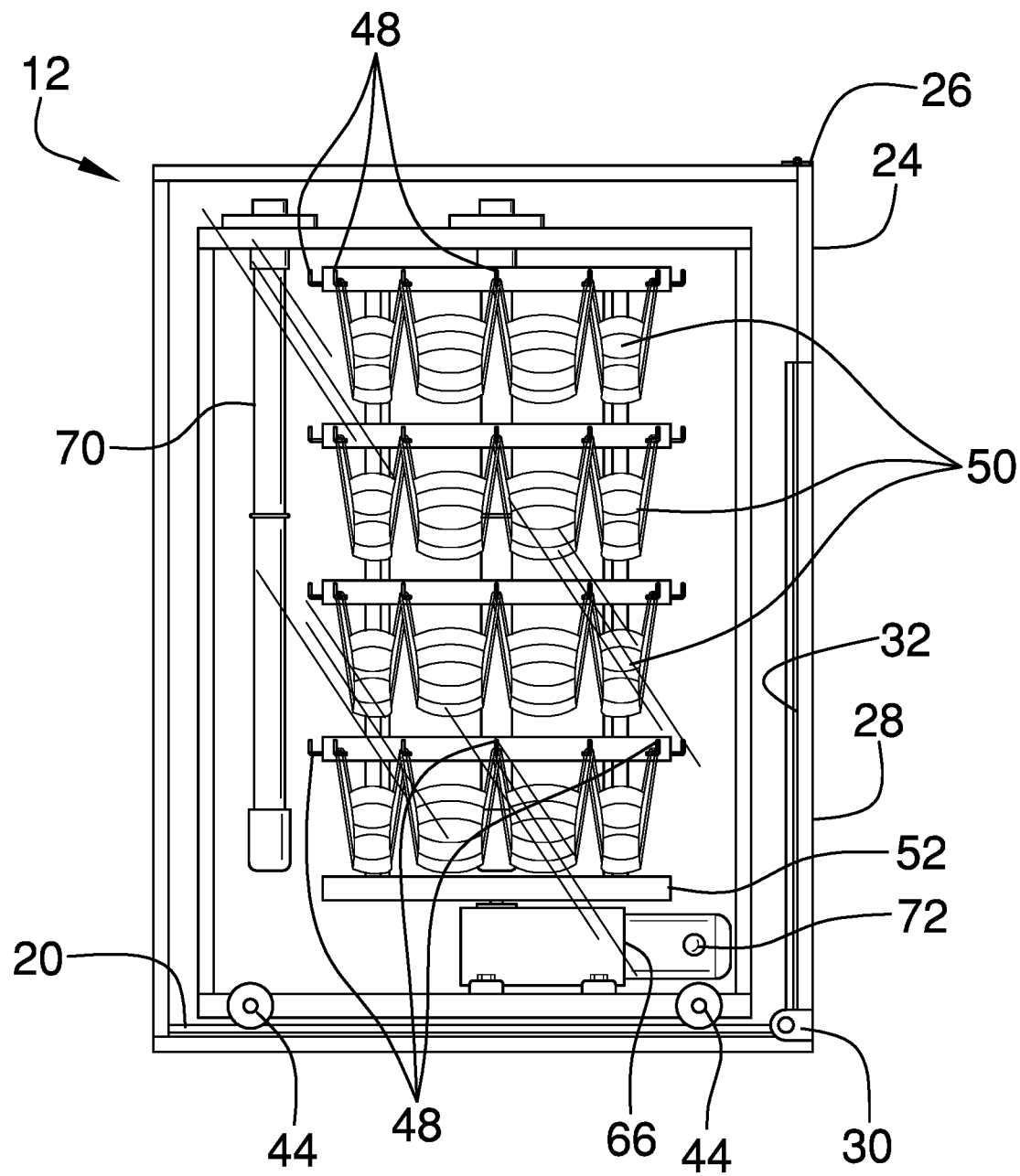
FIG. 8 is a perspective in-use view of an embodiment of the disclosure.

With reference now to the drawings, and in particular to FIGS. 1 through 8 thereof, a new sanitizing device embodying the principles and concepts of an embodiment of the disclosure and generally designated by the reference numeral 10 will be described.

As best illustrated in FIGS. 1 through 8, the personal protective equipment sanitizing assembly 10 generally comprises a cabinet 12 is comprised of a translucent material to pass light therethrough. The cabinet 12 has a bottom wall 14, a top wall 16 and a front side 18, and the front side 18 is open to access an interior of the cabinet 12. A pair of first tracks 20 is each coupled to a top surface 22 of the bottom wall 14. The first tracks 20 are spaced apart from each other and terminate at the front side 18 of the cabinet 12. An upper door 24 is hingedly coupled to the cabinet 12 and the upper door 24 has an upper edge 26 that is aligned with the top wall 16 of the cabinet 12. The upper door 24 lies against the front side 18 of the cabinet 12 having the upper door 24 extending toward the bottom wall 14 when the upper door 24 is in a closed position.

A lower door 28 is hingedly coupled to the cabinet 12 and the lower door 28 has a lower edge 30 and a first surface 32. The lower edge 30 is aligned with the bottom wall 14 of the cabinet 12 and the first surface 32 lies on a plane that is coplanar with the top surface 22 of the bottom wall 14 of the cabinet 12 when the lower door 28 is in an open position. The first surface 32 lies against the front side 18 of the cabinet 12 and the lower door 28 extends toward the top wall 16 of the cabinet 12 when the lower door 28 is in a closed position. A pair of second tracks 34 is each coupled to the first surface 32 of the lower door 28 and each of the second tracks 34 is aligned with a respective one of the first tracks 20 when the lower door 28 is in the open position.

A cart 36 is provided and the cart 36 is rollably positioned in the cabinet 12, and the cart 36 is rollable onto the lower door 28 when the lower door 28 is opened for accessing the cart 36. The cart 36 has a bottom wall 38, a top wall 40 and a plurality of supports 42 extending therebetween. A plurality of rollers 44 is each rotatably coupled to the cart 36 thereby facilitating the cart 36 to be rolled into or out of the cabinet 12. Each of the rollers 44 is positioned on the bottom wall 38 of the cart 36 and each of the rollers 44 travels along a respective first track 20 and second track 34 when the cart 36 is rolled into or out of the cabinet 12.

A carousel unit 46 is provided and the carousel unit 46 is rotatably coupled to the cart 36. The carousel unit 46 includes a plurality of suspensions 48 to support a respective one of a plurality of face masks 50 or other personal protective equipment. The carousel unit 46 rotates in the cart 36 when the carousel unit 46 is turned on to rotate the plurality of face masks 50 in the cart 36. The carousel unit 46 comprises a disk 52 that has an upper surface 54 and a lower surface 56. The carousel unit 46 includes a plurality of members 58 and each of the members 58 is coupled to and extends upwardly from the upper surface 54 of the disk 52 such that each of the members 58 is vertically oriented in the cart 36. Each of the members 58 has a distal end 60 with respect to the disk 52 and the members 58 are spaced apart from each other and are distributed around a perimeter of the disk 52.

The carousel unit 46 includes a plurality of rings 62 that each has an outwardly facing surface 64. Each of the rings 62 is coupled to the plurality of members 58 has each of the rings 62 lying on a plane that is oriented coplanar with the upper surface 54 of the disk 52. The rings 62 are spaced apart from each other and are distributed between the disk 52 and the distal end 60 of the members 58. Each of the suspensions 48 is coupled to the outwardly facing surface 64 of a respective one of the rings 62. Moreover, the suspensions 48 are spaced apart from each other and are distributed around the outwardly facing surface 64 of the rings 62.

A motor 66 is coupled to the bottom wall 38 of the cart 36 and the motor 66 has an output shaft 68 that is coupled to the lower surface 56 of the disk 52. The motor 66 rotates the disk 52 about an axis extending through the upper surface 54 and the lower surface 56 of the disk 52 when the motor 66 is turned on to transport the plurality of face masks 50 in a circle. The motor 66 may comprise an electric motor or the like.

A plurality of light emitters 70 is each coupled to the cart 36 to emit light onto the carousel unit 46. Each of the light emitters 70 has an operational wavelength ranging between approximately 10.0 nm and 400.0 nm to emit ultraviolet light for sterilizing the face masks 50. Each of the light emitters 70 extends downwardly from a lower surface 71 of the top wall 16 of the cart 36. A respective one of the light emitters 70 extends downwardly through each of the rings 62. A respective plurality of the light emitters 70 is spaced from the outwardly facing surface 64 of the rings 62.

A power button 72 is coupled to the cart 36. The power button 72 is electrically coupled to the motor 66 and each of the light emitters 70. The power button 72 turns the motor 66 and each of the light emitters 70 on and off. A power supply 74 is positioned on the cart 36, the power supply 74 is electrically coupled to the power button 72 and the power supply 74 comprises at least one battery.

In use, the face masks 50 are each hung on a respective suspension 48 and the cart 36 is slid into the cabinet 12. Each of the upper door 24 and the lower door 28 are closed and the power button 72 is manipulated to turn on the motor 66 and the light emitters 70. In this way the face masks 50 are sterilized while the face masks 50 are stored in the cabinet 12. Thus, the face masks 50 can be worn by multiple people without the fear of infectious transmission. The face masks 50 can additionally be stored in the sterile environment produced in the cabinet 12 for extended periods of time.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A personal protective equipment sanitizing assembly for storing a sanitizing PPE for reuse, said assembly comprising:
    a cabinet being comprised of a translucent material wherein said cabinet is configured to pass light therethrough;
    an upper door being hingedly coupled to said cabinet;
    a lower door being hingedly coupled to said cabinet;
    a cart being rollably positioned in said cabinet, said cart being rollable onto said lower door when said lower door is opened for accessing said cart;
    a plurality of rollers, each of said rollers being rotatably coupled to said cart thereby facilitating said cart to be rolled into or out of said cabinet;
    a carousel unit being rotatably coupled to said cart, said carousel unit including a plurality of suspensions wherein each of said suspensions is configured to support a respective one of a plurality of face masks or other personal protective equipment, said carousel unit rotating in said cart when said carousel unit is turned on wherein said carousel unit is configured to rotate the plurality of face masks in said cart; and
    a plurality of light emitters, each of said light emitters being coupled to said cart wherein each of said light emitters is configured to emit light onto said carousel unit, each of said light emitters having an operational wavelength ranging between approximately 10.0 nm and 400.0 nm wherein said light emitters are configured to emit ultraviolet light for sterilizing the face masks.

2. The assembly according to claim 1, wherein:
said cabinet has a bottom wall, a top wall and a front side, said front side being open to access an interior of said cabinet; and
said assembly includes a pair of first tracks, each of said first tracks being coupled to a top surface of said bottom wall, said first tracks being spaced apart from each other and terminating at said front side of said cabinet.

3. The assembly according to claim 2, further comprising said upper door having an upper edge being aligned with said top wall of said cabinet, said upper door lying against said front side of said cabinet having said upper door extending toward said bottom wall when said upper door is in a closed position.

4. The assembly according to claim 2, wherein said lower door has a lower edge and a first surface, said lower edge being aligned with said bottom wall of said cabinet, said first surface lying on a plane being coplanar with said top surface of said bottom wall of said cabinet when said lower door is in an open position, said first surface lying against said front side of said cabinet having said lower door extending toward said top wall of said cabinet when said lower door is in a closed position.

5. The assembly according to claim 4, further comprising a pair of second tracks, each of said second tracks being coupled to said first surface of said lower door, each of said second tracks being aligned with a respective one of said first tracks when said lower door is in said open position.

6. The assembly according to claim 5, wherein:
said cart has a bottom wall, a top wall and a plurality of supports extending therebetween; and
each of said rollers is positioned on said bottom wall of said cart, each of said rollers traveling along a respective first track and second track when said cart is rolled into or out of said cabinet.

7. The assembly according to claim 1, wherein said carousel unit comprises:
a disk having an upper surface and a lower surface; and
a plurality of members, each of said members being coupled to and extending upwardly from said upper surface of said disk such that each of said members is vertically oriented in said cart, each of said members having a distal end with respect to said disk, said members being spaced apart from each other and being distributed around a perimeter of said disk.

8. The assembly according to claim 7, wherein said carousel unit includes a plurality of rings, each of said rings having an outwardly facing surface, each of said rings being coupled to said plurality of members having each of said rings lying on a plane being oriented coplanar with said upper surface of said disk, said rings being spaced apart from each other and being distributed between said disk and said distal end of said members.

9. The assembly according to claim 8, wherein each of said suspensions is coupled to said outwardly facing surface of a respective one of said rings, said suspensions being spaced apart from each other and being distributed around said outwardly facing surface of said rings.

10. The assembly according to claim 8, wherein said carousel unit includes a motor being coupled to said bottom wall of said cart, said motor having an output shaft being coupled to said lower surface of said disk, said motor rotating said disk about an axis extending through said upper surface and said lower surface of said disk when said motor is turned on wherein said rings are configured to transport the plurality of face masks in a circle.

11. The assembly according to claim 8, wherein each of said light emitters extends downwardly from a lower surface of a top wall of said cart, a respective one of said light emitters extending downwardly through each of said rings, a respective plurality of said light emitters being spaced from said outwardly facing surface of said rings.

12. The assembly according to claim 11, wherein:
said carousel unit includes a motor; and
said assembly includes a power button being coupled to said cart, said power button being electrically coupled to said motor and each of said light emitters, said power button turning said motor and each of said light emitters on and off.

13. The assembly according to claim 12, further comprising a power supply being positioned on said cart, said power supply being electrically coupled to said power button, said power supply comprising at least one battery.

14. A personal protective equipment sanitizing assembly for storing a sanitizing PPE for reuse, said assembly comprising:
a cabinet being comprised of a translucent material wherein said cabinet is configured to pass light therethrough, said cabinet having a bottom wall, a top wall and a front side, said front side being open to access an interior of said cabinet;
a pair of first tracks, each of said first tracks being coupled to a top surface of said bottom wall, said first tracks being spaced apart from each other and terminating at said front side of said cabinet;
an upper door being hingedly coupled to said cabinet, said upper door having an upper edge being aligned with said top wall of said cabinet, said upper door lying against said front side of said cabinet having said upper door extending toward said bottom wall when said upper door is in a closed position;
a lower door being hingedly coupled to said cabinet, said lower door having a lower edge and a first surface, said lower edge being aligned with said bottom wall of said cabinet, said first surface lying on a plane being coplanar with said top surface of said bottom wall of said cabinet when said lower door is in an open position, said first surface lying against said front side of said cabinet having said lower door extending toward said top wall of said cabinet when said lower door is in a closed position;
a pair of second tracks, each of said second tracks being coupled to said first surface of said lower door, each of said second tracks being aligned with a respective one of said first tracks when said lower door is in said open position;
a cart being rollably positioned in said cabinet, said cart being rollable onto said lower door when said lower door is opened for accessing said cart, said cart having a bottom wall, a top wall and a plurality of supports extending therebetween;
a plurality of rollers, each of said rollers being rotatably coupled to said cart thereby facilitating said cart to be rolled into or out of said cabinet, each of said rollers being positioned on said bottom wall of said cart, each of said rollers traveling along a respective first track and second track when said cart is rolled into or out of said cabinet;
a carousel unit being rotatably coupled to said cart, said carousel unit including a plurality of suspensions wherein each of said suspensions is configured to support a respective one of a plurality of face masks or other personal protective equipment, said carousel unit rotating in said cart when said carousel unit is turned on wherein said carousel unit is configured to rotate the plurality of face masks in said cart, said carousel unit comprising:
- a disk having an upper surface and a lower surface;
- a plurality of members, each of said members being coupled to and extending upwardly from said upper surface of said disk such that each of said members is vertically oriented in said cart, each of said members having a distal end with respect to said disk, said members being spaced apart from each other and being distributed around a perimeter of said disk;
- a plurality of rings, each of said rings having an outwardly facing surface, each of said rings being coupled to said plurality of members having each of said rings lying on a plane being oriented coplanar with said upper surface of said disk, said rings being spaced apart from each other and being distributed between said disk and said distal end of said members, each of said suspensions being coupled to said outwardly facing surface of a respective one of said rings, said suspensions being spaced apart from each other and being distributed around said outwardly facing surface of said rings; and
- a motor being coupled to said bottom wall of said cart, said motor having an output shaft being coupled to said lower surface of said disk, said motor rotating said disk about an axis extending through said upper surface and said lower surface of said disk when said motor is turned on wherein said rings are configured to transport the plurality of face masks in a circle;
- a plurality of light emitters, each of said light emitters being coupled to said cart wherein each of said light emitters is configured to emit light onto said carousel unit, each of said light emitters having an operational wavelength ranging between approximately 10.0 nm and 400.0 nm wherein said light emitters are configured to emit ultraviolet light for sterilizing the face masks, each of said light emitters extending downwardly from a lower surface of said top wall of said cart, a respective one of said light emitters extending downwardly through each of said rings, a respective plurality of said light emitters being spaced from said outwardly facing surface of said rings;
- a power button being coupled to said cart, said power button being electrically coupled to said motor and each of said light emitters, said power button turning said motor and each of said light emitters on and off; and
- a power supply being positioned on said cart, said power supply being electrically coupled to said power button, said power supply comprising at least one battery.

* * * * *